United States Patent
Quistgaard et al.

(10) Patent No.: US 7,695,437 B2
(45) Date of Patent: Apr. 13, 2010

(54) ULTRASOUND THERAPY HEAD WITH MOVEMENT CONTROL

(75) Inventors: Jens U. Quistgaard, Seattle, WA (US); Tim Etchells, Bothell, WA (US); Gregory Paul Darlington, Snohomoish, WA (US); Charles S. Desilets, Edmonds, WA (US)

(73) Assignee: Medicis Technologies Corporation, Bothell, WA (US)

( * ) Notice: Subject to any disclaimer, the term of this patent is extended or adjusted under 35 U.S.C. 154(b) by 659 days.

(21) Appl. No.: 11/027,912

(22) Filed: Dec. 29, 2004

(65) Prior Publication Data

US 2005/0187495 A1 Aug. 25, 2005

Related U.S. Application Data

(60) Provisional application No. 60/534,036, filed on Dec. 30, 2003.

(51) Int. Cl.
*A61B 8/00* (2006.01)

(52) U.S. Cl. .............. 600/446; 600/437; 600/443; 600/444; 600/445; 601/2; 601/3; 601/4

(58) Field of Classification Search ............. 600/437, 600/439, 444; 601/2, 3, 4
See application file for complete search history.

(56) References Cited

U.S. PATENT DOCUMENTS

| 4,002,221 A | 1/1977 | Buchalter |
| 4,059,098 A | 11/1977 | Murdock |
| 4,211,949 A | 7/1980 | Brisken et al. |
| 4,291,578 A | 9/1981 | Hetz et al. |
| 4,326,418 A | 4/1982 | Pell, Jr. |
| 4,368,410 A | 1/1983 | Hance et al. |
| 4,437,033 A | 3/1984 | Diepers |
| 4,459,854 A | 7/1984 | Richardson et al. |
| 4,501,557 A | 2/1985 | Tamura et al. |
| 4,556,066 A | 12/1985 | Semrow |
| 4,567,895 A * | 2/1986 | Putzke ................ 600/445 |
| 4,593,699 A | 6/1986 | Poncy et al. |

(Continued)

FOREIGN PATENT DOCUMENTS

GB          820814          9/1959

OTHER PUBLICATIONS

Ayme et al., Occurance of transient cavitation in pulsed swatooth ultrasonic fields *J. Acoust Soc. Am.* (1988) 84(5):1598-1605.

(Continued)

*Primary Examiner*—Brian Casler
*Assistant Examiner*—John F Ramirez
(74) *Attorney, Agent, or Firm*—Townsend and Townsend and Crew LLP

(57) ABSTRACT

A therapy head for use in HIFU procedures is described. The therapy head has an enclosure with a window, an energy applicator and a means of moving the energy applicator within the enclosure. The therapy head uses motors and actuators to move the energy applicator, usually an ultrasound transducer, inside the enclosure. A controller is provided either internally or externally that allows the therapy head to identify and distinguish locations where the therapy head should be to radiate energy into a patient. The controller uses the motors and actuators to move the energy applicator into the desired locations.

17 Claims, 4 Drawing Sheets

U.S. PATENT DOCUMENTS

| | | | |
|---|---|---|---|
| 4,865,042 | A | 9/1989 | Umemura et al. |
| 4,960,107 | A | 10/1990 | Aida et al. |
| 5,259,383 | A | 11/1993 | Holstein et al. |
| 5,301,660 | A | 4/1994 | Rattner |
| 5,352,301 | A | 10/1994 | Panchanathan et al. |
| 5,382,286 | A | 1/1995 | Fanning et al. |
| 5,419,327 | A * | 5/1995 | Rohwedder et al. ......... 600/439 |
| 5,434,208 | A | 7/1995 | Batelaan et al. |
| 5,476,438 | A | 12/1995 | Edrich et al. |
| 5,477,736 | A | 12/1995 | Lorraine |
| 5,505,206 | A | 4/1996 | Walloch |
| 5,526,815 | A | 6/1996 | Granz et al. |
| 5,568,810 | A | 10/1996 | Hamers et al. |
| 5,623,928 | A | 4/1997 | Wright et al. |
| 5,626,554 | A | 5/1997 | Ryaby et al. |
| 5,669,150 | A | 9/1997 | Guertin et al. |
| 5,676,159 | A | 10/1997 | Navis |
| 5,738,098 | A | 4/1998 | Brock-Fisher et al. |
| 5,738,635 | A | 4/1998 | Chapelon et al. |
| 5,755,753 | A | 5/1998 | Knowlton |
| 5,769,790 | A | 6/1998 | Watkins et al. |
| 5,820,623 | A | 10/1998 | Ng |
| 5,871,446 | A | 2/1999 | Wilk |
| 5,938,608 | A | 8/1999 | Bieger et al. |
| 5,938,922 | A | 8/1999 | Fulk, Jr. et al. |
| 6,039,689 | A | 3/2000 | Lizzi |
| 6,039,694 | A | 3/2000 | Larson et al. |
| 6,085,749 | A | 7/2000 | Wardle et al. |
| 6,113,558 | A | 9/2000 | Rosenschein et al. |
| 6,142,748 | A | 11/2000 | Harris et al. |
| 6,152,137 | A | 11/2000 | Schwartz et al. |
| 6,217,515 | B1 | 4/2001 | Yamakawa et al. |
| 6,233,476 | B1 | 5/2001 | Strommer et al. |
| 6,261,249 | B1 | 7/2001 | Talish et al. |
| 6,264,605 | B1 | 7/2001 | Scirica et al. |
| 6,302,848 | B1 | 10/2001 | Larson et al. |
| 6,306,146 | B1 | 10/2001 | Dinkler |
| 6,350,245 | B1 | 2/2002 | Cimino |
| 6,366,831 | B1 | 4/2002 | Raab |
| 6,419,648 | B1 * | 7/2002 | Vitek et al. .................... 601/3 |
| 6,423,077 | B2 | 7/2002 | Carol et al. |
| 6,488,639 | B1 | 12/2002 | Ribault et al. |
| 6,506,171 | B1 | 1/2003 | Vitek et al. |
| 6,554,826 | B1 | 4/2003 | Deardorff |
| 6,561,389 | B1 | 5/2003 | Earle |
| 6,575,906 | B1 | 6/2003 | Schembri, Jr. et al. |
| 6,607,498 | B2 | 8/2003 | Eshel |
| 6,613,004 | B1 | 9/2003 | Vitek et al. |
| 6,618,620 | B1 | 9/2003 | Freundlich et al. |
| 7,255,678 | B2 * | 8/2007 | Mehi et al. .................. 600/446 |
| 2002/0128592 | A1 | 9/2002 | Eshel |
| 2003/0004439 | A1 | 1/2003 | Pant et al. |
| 2003/0083536 | A1 | 5/2003 | Eshel et al. |

OTHER PUBLICATIONS

Clarke et al.. Physical and chemical aspects of ultrasonic disruption of cells *J. Acoust. Soc. Am.* (1970) 47(2):649-653.

Flynn et al., A mechanism for the generation of cavitation maxima by pulsed ultrasound *J. Acoust Soc. Am.* (1984) 76(2):505-512.

Fry et al., Threshold ultrasonic dosages for structural changes in the mammalian brain *J. Acoust. Soc. Am.* (1970) 48(6):1413-1417.

Kinney, Body contouring with external ultrasound *Plastic & Reconstruct.* Surg. (1999) 103:728-729.

Padmaker, Thresholds and mechanisms of ultrasonic damage to 'organized' animal tissues *Symposium on Biological Effects and Characterizations of Ultrasound Sources* (1977) Hazzard et al., Eds., pp. 224-239.

Kinney, "Body Contouring with External Ultrasound, " *Plastic & Reconstructive Surgery*, (Feb. 1999),vol. 103, No. 2, pp. 728-729.

Lele, "Thresholds and mechanisms of ultrasonic damage to "organized" animal tissues, "Proc Symp Biol Eff Character Ultrasound Sources, (Jun. 2-3, 1977), Rockville, Maryland, (Dec. 1977), pp. 224-239.

Adams et al., "Chronic Response of Normal Porcine Fat and Muscle to Focused Ultrasound Hyperthermia,"*Radiation Research*, (1985), vol. 104, pp. 140-152.

Ayme et al., "Occurence of Transient Cavitation in Pulsed Sawtooth Ultrasonic Fields," *J. Acoust. Soc. Am.*, (Nov. 1988), vol. 84, No. 5, pp. 1598-1605.

Billard et al., "Effects of Physical Parameters on High Temperature Ultrasound Hyperthermia," *Ultrasound Med Biol.*, (1990), vol. 16, No. 4, pp. 409-420.

Chen et al., "Mechanisms of Lesion Formation in High Intensity Focused Ultrasound Therapy," *Proc. IEEE Ultrason. Symp.*, (Oct. 2002), vol. 2, pp. 1443-1446.

Chongqing Haifu (Hifu) Technology Co., LTD., [Brochure], "Haifu: Brief Introduction of the Company," pp. 1-26.

Clarke et al., "Physical and Chemical Aspects of Ultrasonic Disruption of Cells," *J. Acoust. Soc. Am.*, (Feb. 1970), vol. 47, No. 2B, pp. 649-653.

Fjield et al., "In Vivo Verification of the Acoustic Model Used to Predict Temperature Elevations for MRI Guided Ultrasound Surgery," *Proc. IEEE Ultrason. Symp.*, (1998), vol. 2, pp. 1415-1418.

Flynn et al, "A Mechanism for the Generation of Cavitation Maxima by Pulsed Ultrasound, "*J. Acoust. Soc. Am.*, (Aug. 1984), vol. 76, No. 2, pp. 505-512.

Fry et al., "Threshold Ultrasonic Dosages for Structural Changes in the Mammalian Brain," *Acoust. Soc. Am.*, (Dec. 1970), vol. 48, No. 6B, pp. 1413-1417.

Haar, "Ultra sound Focal Beam Surgery," *Ultrasound Med Biol.*, (1995), vol. 21, No. 9, pp. 1089-1100.

Hand, "Ultrasound Hyperthermia and the Prediction of Heating,"Chapter 8, *Ultrasound in Medicine*, eds. Duck et al., Inst of Physics Pub Inc, Bristol, (Dec. 1998), pp. 151-157.

Hoffelner et al., "Self-Focusing HIFU Source for Large Therapy Volumes," Ultrasonics Symposium, *Proc. IEEE Ultrason. Symp* (1998), vol. 2, pp. 1563-1566.

* cited by examiner

ULTRASOUND THERAPY HEAD WITH MOVEMENT CONTROL

CROSS-REFERENCES TO RELATED APPLICATIONS

This application claims the benefit of provisional application No. 60/534,036, filed on Dec. 30, 2003, the full disclosure of which is incorporated herein by reference.

The subject matter of the present application is related to that of the following applications: Ser. No. 10/750,370, entitled "Medical Device Inline Degasser"; Ser. No. 10/751,344, entitled "Articulating Arm for Medical Procedures"; Ser. No. 10/750,369, entitled "Disposable Transducer Seal"; 60/533,528, entitled "Position Tracking Device"; 60/533,988, entitled "Method for Planning and Performing Ultrasound Therapy"; 60/533,958, entitled "Systems and Methods for the Destruction of Adipose Tissue"; 60/534,034, entitled "Component Ultrasound Transducer"; the full disclosure of each of these applications are incorporated herein by reference.

BACKGROUND OF THE INVENTION

1. Field of the Invention

The present invention relates to a handheld medical device for delivering energy in precise locations into the human body. The device is principally for non-invasive therapies.

2. Background of the Present Invention

A general problem in the application of high intensity focused ultrasound (HIFU) for therapeutic purposes is that it is often necessary to hold the therapeutic means stationary for some significant amount of time over the tissue to be treated. Alternatively, it may be necessary to scan the therapy beam at a slow, constant rate through the tissue to be treated. Both of these requirements present a barrier to a hand-held therapeutic device, as it is often difficult or impossible for a person to either hold the device steady, or to scan at an acceptably slow and steady rate for the desired therapeutic effect.

A HIFU procedure may require that the ultrasound beam be scanned over the treatment volume at a constant rate (e.g. 5 mm/sec +/−1 mm/sec) to achieve the desired therapeutic effect. Additionally, the treatment volume must be scanned so that there is never more than a 2 mm spacing between adjacent focal lines of treatment. These requirements are beyond the capabilities of human beings. The solution in the past has been to incorporate a computer controlled motion device rigidly mounted to something that is stationary with respect to the patient (e.g. the floor, wall or bed). Such a device is either absolutely stationary, or is able to scan at a precise rate in a precise pattern without any human intervention. Such an arrangement has the disadvantages of size and bulk, complexity and reliability of the overall device.

Thus there remains a need in the art for a HIFU applicator that can be easily manipulated by a user while still providing reliable and uniform treatment.

There is also a need for a HIFU transducer that can keep track of the tissue volumes treated so as to prevent re-treatment of those same volumes.

There is still further a need for a therapy device that can assist the operator in identifying regions of tissue to be treated.

BRIEF SUMMARY OF THE INVENTION

It is an objective of the present invention to provide for a therapy head usable in HIFU procedures that can be easily manipulated and provide reliable and uniform treatment.

It is another object of the presenting invention to track tissue in a library or map of the tissue to be treated.

It is still further an objective of the present invention to provide a means for alerting a physician to any problems or difficulties associated with a procedure using a HIFU generator of the present invention.

At least some of the objectives of the present invention are realized through an ultrasound therapy head comprising an enclosure having a window, at least one energy applicator suspended within the enclosure and a means for maneuvering the energy applicator within the enclosure such that the energy applicator radiates energy through the window.

Preferably the energy applicator is an ultrasound transducer however a variety of other energy applicator may be used in combination with an ultrasound transducer.

The means for maneuvering the energy applicator preferably includes a means for determining the position of the energy applicator within the enclosure.

DETAILED DESCRIPTION OF THE INVENTION

Figure 1:
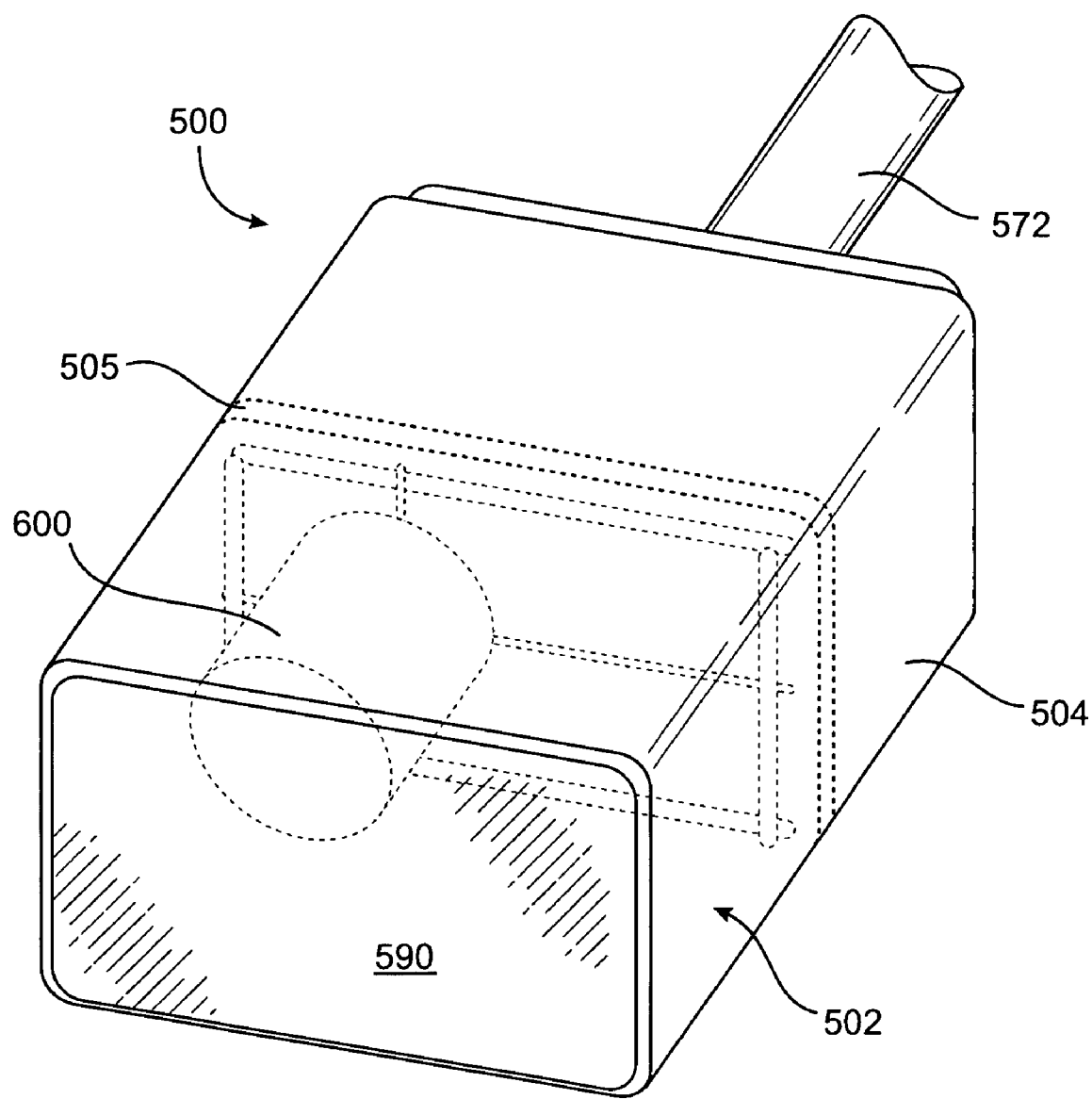
FIG. 1 illustrates a therapy head.

Described herein is a device for use primarily in high intensity ultrasound procedures. A therapy head is disclosed having an enclosure with a window. The enclosure contains one or more energy applicators, and a means of moving the energy applicators within the enclosure. The energy applicators are positioned so the radiant energy passes through the window to a patient.

The enclosure is preferably small enough to be manipulated by hand. It can be operated by itself with a physician carrying the load of the therapy head, or it can be supported by an articulating arm or other mechanical device. The enclosure has a window that is oriented toward a patient. The window may be made from any material so long as it is essentially transparent to the energy applicator. The window may be incorporated into the enclosure, or it may be a removable device. If the window is a removable device, then the window will cover an access port through which the interior components of the enclosure may be accessed. The window may also be a disposable device, such as a disposable transducer seal.

Within the enclosure is at least one energy applicator. Preferably this energy applicator is an ultrasound transducer. More preferably the ultrasound transducer is a high intensity focused ultrasound transducer. However the transducer may be a component transducer assembly, or a device that incorporates multiple energy applicators, some of which may not be ultrasound transducers.

There is a positioner or other means for maneuvering the energy applicator within the enclosure. The means for maneuvering the energy applicator requires two components. A first component is one or more actuators. The energy applicator is attached to the actuators. The attachment may be a slidable engagement, rotational engagement or through a series of traveler rods. The actuators are driven by a force generating device, like an electric motor or the equivalent. Electric motors are preferred for their small size and reliability. One or more position sensing devices, such as rotational or optical encoders, are built into either the motor assembly, or the actuators, so the movement of the energy applicator within the enclosure is known. Alternatively the energy applicator may also contain a miniature location device (e.g. like mini-GPS system) that an external sensor can identify to determine the location of the energy applicator within the enclosure.

The second component of the maneuvering means is a driver or controller. The driver or controller directs the movement of the motors, and thus the movement of the actuators and the maneuvering of the energy applicator. The controller may be a medical appliance, a computer, or a specialized medical procedure controller. The controller may be positioned within the enclosure, or it may be a device outside the enclosure providing signal to the motors.

In operation, the controller has a library of data used to coordinate the movement of the energy applicator and the dosage of the radiant energy into the patient. By controlling the movement of the energy applicator while radiant energy is emitted through the window, a precise energy dosage may be delivered into the patient. The controller can be programmed with the parameters needed to perform the task. Parameters may include the type of therapy to be administered and the maximum safe dosage that may be applied to a patient for a given area, volume or mass of tissue.

Once the therapy head has been completely prepared for a procedure, a physician can place the therapy head on a patient. The therapy head can move the energy applicator within the enclosure to treat the patient according to the procedure parameters programmed into the controller. If the procedure area is small, then the controller can move and activate the energy emitter without any additional input from a user.

If the treatment area exceeds the window of the enclosure, or exceeds the range of motion of the energy applicator within the enclosure, the therapy head must be moved to cover as much area as needed. Movement of the therapy head can be done manually, or through a mechanical device. Data from the encoders is relayed to the controller so that the controller can identify the position of the energy applicator within the confines of the enclosure. This position information can be combined with a Position Tracking Device (Co-pending application, Ser. No. 11/027,911), and an Articulating Arm (Co-pending application, Ser. No. 11/751,344). The controller can utilize position data from the present invention, combined with the data derived from the two aforementioned co-pending applications, to produce precise position data for the energy applicator with respect to the enclosure, the patient and a fixed external reference point. During the procedure if the controller reads the position or motion information from the encoders and other sensors and determines the energy applicator is not in the proper position, the controller can use the means for maneuvering the applicator, to correct the energy applicator's position.

Similarly the controller can identify the dosage of energy delivered with great precision to any particular area. The controller can track the amount of energy transmitted into the patient through out the treatment area and can cause the energy applicator to radiate or not radiate depending on the amount of energy already deposited into the patient at the particular place in the procedure.

Turning now to the drawings, in FIG. 1 there is shown a therapy head 500 having an enclosure. The enclosure has a partition 505 and divides the enclosure into an upper chamber 504, and a lower chamber 502. Contained within the lower chamber 502 is an energy applicator 600. The energy applicator 600 is preferably one or more ultrasound transducer(s).

The upper chamber 504 contains a motor assembly. There are one or more pass through ports in the partition 505 allowing position control of the energy applicator from the motor assembly. The pass through ports may also be used for electronic communication between the transducer(s) and a computer 400 and/or therapy controller 250. Electronic communication between the therapy head 500 and the computer 400 and/or therapy controller 250 is achieved through an electronic link 572.

Figure 2:
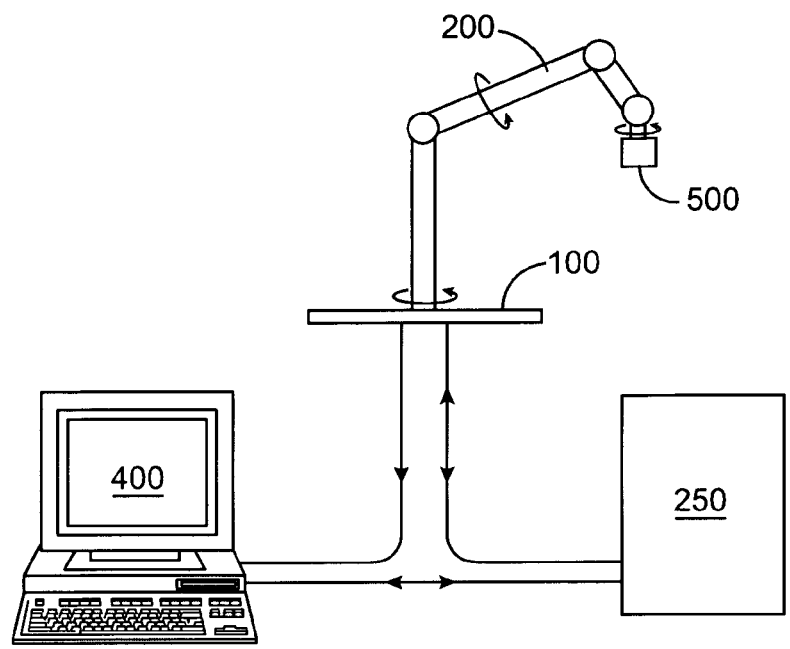
FIG. 2 shows a therapy head on an articulating arm with external control elements.

The therapy head 500 may be mounted (FIG. 2) on an articulated arm 200 supported by a base 100. The articulating arm 200 would also have its movements and functions monitored or controlled by a computer 400 or therapy controller 250.

Figure 3A:
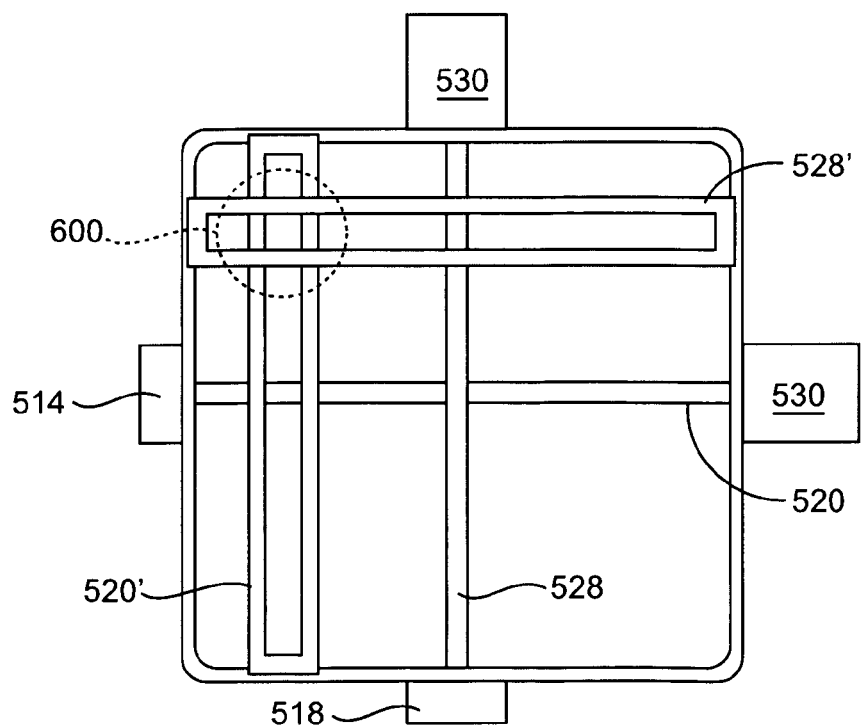
FIGS. 3A-B show internal views of actuators and motors in the therapy head.

Positioning of the energy applicator 600 may be achieved through various different means. A generic representation of a mechanical solution is shown in Fig. 3A. The schematic is a bottom view of the lower chamber 502 without the confining walls of the body of the therapy head. The motors previously described are not shown in this view. A mechanical connection between the motors and the energy applicator can be achieved through a gear assembly or mechanical linkage (referred to hereinafter as a gear linkage). The gear linkages 514, 518 are connected to a pair of travelers rods 520, 528. The traveler rods may act as drive screws for a pair of slotted actuators 520', 528'. Rotation of the traveler rods will cause the corresponding slotted actuator to move, with the energy applicator moving with the intersection of the two slotted actuators. The energy applicator 600 can be positioned anywhere the intersection of the two slotted actuators can be moved. A rotational encoder 530 is attached to each of the traveler rods 520, 528 so the amount of motion can be determined. The data from the rotational encoders is used by a computer to determine and plan the movement and energy transmission into the patient.

Figure 3B:
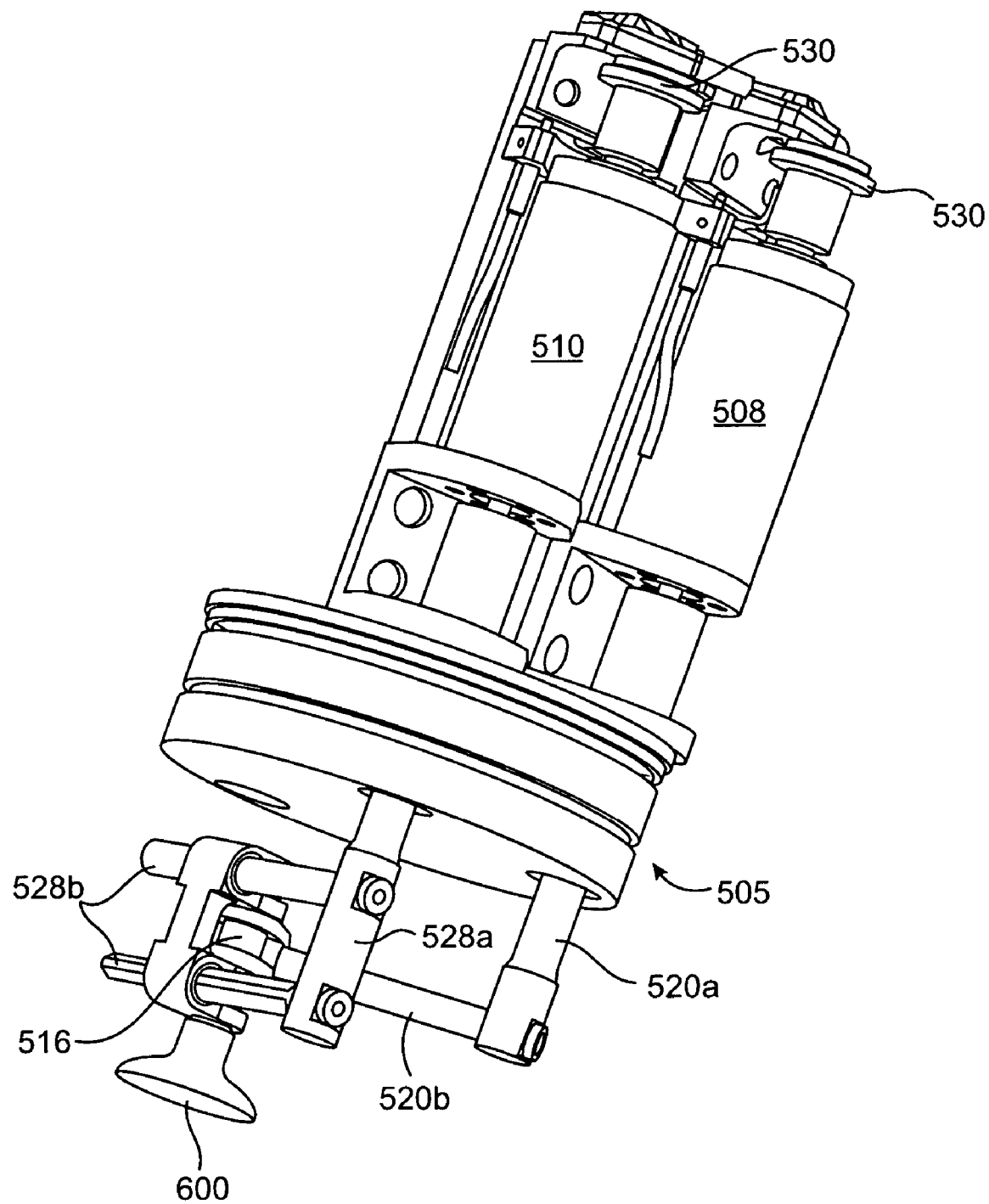

In the preferred embodiment FIG. 3B), motor drives 508, 510 are connected to direct couplers 520a, 528a instead of a pair of traveler rods 520, 528 as previously described. The direct couplers 520a, 528a are connected to a pair of pivoting sliders 520b, 528b. A transducer carriage 516 is mounted with a plurality of angular joint receptacles allowing the transducer carriage 516 to move with the pivoting slides 520b, 528b. In this manner as the pivoting slides change the angle of intersection relative to each other, the transducer carriage is able to move with the intersection of the sliders, thus providing movement control of the transducer carriage 516 in the lower chamber. A transducer 600 or other radiant energy device is mounted on the transducer carriage 516. A rotational encoder 530 is mounted on each of the motors 508, 510 to measure the true rotation of each of the direct couplers 520a, 528a. The encoders 530, motors 508, 510, and transducer 600 are all in electronic communication with the computer 400 and/or therapy processor 250 so the precise location of the transducer within the lower chamber 502 can be determined at any time.

Figure 4:
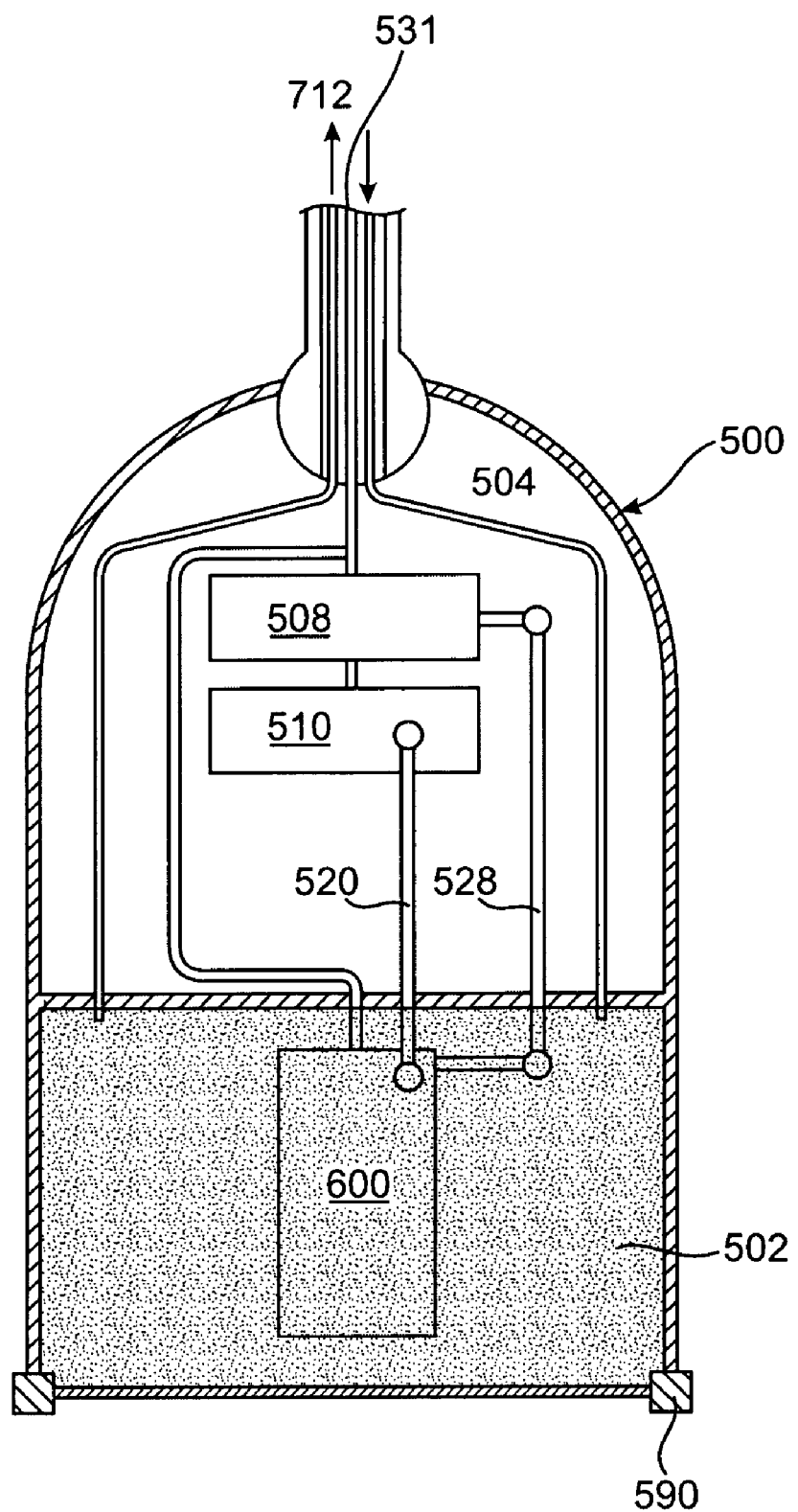
FIG. 4 provides a schematic of the elements of the present invention.

FIG. 4 illustrates a schematic of the present invention. The enclosure defined by the interior of the therapy head 500 is separated into an upper chamber 504 and a lower chamber 502. The partition 505 between the upper chamber 504 and lower chamber 502 has a plurality of pass through ports for the mechanical connections 520, 528 between the motors 508, 510 and the transducer 600. Fluid flows through a fluid circuit 712 and electronic communication is provided through an electronic communication link 531. The therapy head 500 is closed off with a transmissible window 590.

What is claimed is:

1. A therapy head comprising:
   an enclosure having a window, said enclosure adapted to be manipulated by hand;
   at least one directional energy applicator suspended within said enclosure; and
   a positioner programmed to maneuver the energy applicator within said enclosure, the positioner, comprising:
      a first motor connected to a first traveler rod, the first traveler rod mechanically engaged to a first actuator;
      a second motor connected to a second traveler rod, the second traveler rod mechanically engaged to a second actuator wherein the actuators are arranged to form an intersection between said first and second actuator, the directional energy applicator being movably positioned at the intersection of said first and second actuator;
      wherein the positioner maneuvers the energy applicator to emit radiant energy through the window in order to deliver a precise energy dosage to patient tissue adjacent the window, and wherein the positioner is adapted to maneuver the energy application along a first axis controlled by said first motor and along a second axis controlled by said second motor, the second axis being perpendicular to the first axis.

2. The therapy head of claim 1, wherein said window is a transmissible window for said energy applicator.

3. The therapy head of claim 1, wherein said energy applicator is an ultrasound transducer.

4. The energy applicator of claim 3, wherein said ultrasound transducer is a high intensity focused ultrasound transducer.

5. The therapy head of claim 1, wherein the energy applicator is a component ultrasound transducer.

6. The therapy head of claim 1, wherein the positioner for maneuvering said energy applicator includes one or more position sensors.

7. The therapy head of claim 1, wherein said window is a disposable transducer seal.

8. The therapy head as described in claim 1, wherein said positioner further comprising a plurality of encoders for measuring movement within said enclosure.

9. The therapy head of claim 1, wherein said motors are electric motors.

10. The ultrasound head of claim 1, wherein said positioner further comprises a plurality of encoders.

11. The therapy head of claim 1, wherein said enclosure further comprises a horizontal water tight partition defining an upper enclosure and a lower enclosure, said upper enclosure containing said means for maneuvering and said lower enclosure containing said energy applicator, said window being in said lower enclosure.

12. The therapy head of claim 11, further comprising a fluid circulation system for circulating a coupling fluid through said lower enclosure.

13. A system for directional application of energy over a body surface, the system comprising:
   the therapy head of claim 1; and
   a controller adapted for controlling movement of the energy applicator within the enclosure.

14. The system of claim 13, wherein the controller is further adapted to control dosage delivered from the applicator to the tissue.

15. The system of claim 13, wherein said controller includes a library of data used to coordinate movement and dosage.

16. A method of delivering ultrasound energy to a body surface, said method comprising:
   engaging a hand held enclosure against a body surface;
   positioning the enclosure manually over one location on the body surface; and
   controlling a first motor and a second motor connected to a first actuator and a second actuator, respectively, to control the movement of an energy applicator according to a predetermined program within the hand held enclosure while the enclosure remains stationary relative to the body surface,
   wherein controlling the first motor controls the movement of the energy applicator along a first axis and controlling the second actuator controls the movement of the energy applicator along a second axis perpendicular to the first axis.

17. The method of claim 16, further comprising:
   repositioning the enclosure manually to at least one additional location on the body surface and controlling the movement of the energy applicator within the hand held enclosure while the enclosure remains stationary relative to the body surface.

* * * * *